(12) United States Patent
Chaudhuri

(10) Patent No.: US 8,160,347 B2
(45) Date of Patent: Apr. 17, 2012

(54) SYSTEM AND METHOD FOR INTELLIGENT CAD PROCESSING

(75) Inventor: Kallol Chaudhuri, Upper Merion, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 425 days.

(21) Appl. No.: 12/473,350

(22) Filed: May 28, 2009

(65) Prior Publication Data

US 2009/0297013 A1 Dec. 3, 2009

Related U.S. Application Data

(60) Provisional application No. 61/058,280, filed on Jun. 3, 2008.

(51) Int. Cl.
*G06K 9/00* (2006.01)
(52) U.S. Cl. .......................... 382/132; 382/128; 382/130
(58) Field of Classification Search .......... 382/128–132, 382/305; 715/233, 230, 231, 268
See application file for complete search history.

(56) References Cited

U.S. PATENT DOCUMENTS

| | | | | |
|---|---|---|---|---|
| 6,785,410 B2* | 8/2004 | Vining et al. | ................. | 382/128 |
| 6,950,492 B2* | 9/2005 | Besson | ............................ | 378/5 |
| 7,289,651 B2* | 10/2007 | Vining et al. | ................. | 382/128 |
| 7,421,647 B2* | 9/2008 | Reiner | .......................... | 715/230 |
| 7,532,942 B2* | 5/2009 | Reiner | ........................... | 700/90 |
| 7,607,079 B2* | 10/2009 | Reiner | ........................... | 715/233 |

* cited by examiner

*Primary Examiner* — Sang Nguyen
(74) *Attorney, Agent, or Firm* — Peter Withstandley

(57) ABSTRACT

A computer implemented method for automatically selecting an algorithm for image analysis in a computer-aided detection/diagnosis (CAD) system includes receiving image data for a study involving a patient, querying a radiology information system (RIS) for an IHE (Integrating the Healthcare Enterprise)-worklist for the study of the patient, receiving the IHE-worklist from the RIS, analyzing the worklist to select one or more CAD algorithm for analyzing the image data, executing the selected one or more CAD algorithms to analyze the image data, and outputting results of the analysis of the image data.

24 Claims, 2 Drawing Sheets

SYSTEM AND METHOD FOR INTELLIGENT CAD PROCESSING

CROSS REFERENCE TO RELATED UNITED STATES APPLICATIONS

This application claims priority from "IHE-WL Based CAD Processing", U.S. Provisional Application No. 61/058,280 of Kallol Chaudhuri, filed Jun. 3, 2008, the contents of which are herein incorporated by reference in their entirety.

TECHNICAL FIELD

This disclosure is directed to using an IHE-WL to select image analysis algorithms for use with CAD systems.

DISCUSSION OF THE RELATED ART

Different CAD (Computer Aided Detection/Diagnosis) algorithms can be applied to an image dataset in order to detect different possible ailments. For example, both pulmonary embolism CAD and nodule detection CAD algorithms can be applied to a computed tomography (CT) lung data. If the purpose of the CT scan is known, then the appropriate algorithm(s) can be applied. An IHE-WL (worklist) contains a list of exams that need to be performed on a patient. Based on this list, a CAD system can determine what algorithms should be applied to a particular dataset.

IHE, or "Integrating the Healthcare Enterprise", is an international consortium of healthcare professionals and industry founded in 1997 to improve the way computer systems in healthcare share information. IHE aims to create a process through which interoperability of health care systems can be implemented. The group gathers case requirements, identifies available standards, and develops technical guidelines that manufacturers can implement. IHE Profiles provide a common language for purchasers and vendors to discuss the integration needs of healthcare sites and the integration capabilities of healthcare IT products. These profiles offer developers a clear implementation path for communication standards supported by industry partners and carefully documented, reviewed and tested, and provide purchasers a tool that reduces the complexity, cost and anxiety of implementing interoperable systems. Profiles for use in radiology include the Scheduled Workflow (SWF), which integrates ordering, scheduling, imaging acquisition, storage and viewing for Radiology exams, and the Post-Processing Workflow (PWF), which provides worklists, status and result tracking for post-acquisition tasks, such as Computer-Aided Detection or Image Processing. Scheduled workflow is part of the radiology profile.

A radiology information system (RIS) is a computerized database used by radiology departments to store, manipulate and distribute patient radiological data and imagery. The system generally consists of patient tracking and scheduling, result reporting and image tracking capabilities.

A hospital information system (HIS), variously also called clinical information system (CIS) is a comprehensive, integrated information system designed to manage the administrative, financial and clinical aspects of a hospital. It can be composed of one or a few software components with specialty-specific extensions as well as of a large variety of sub-systems in medical specialties.

The IHE generally refers to DICOM standards. However, apart from DICOM, there is at least one more standard that can be used for WL. This is the ICD9 standard promulgated by CMS (Center for Medicare and Medicaid). However, the RIS generally does not enforce any standard but rather offers configurable codes for the WL. Some examples of how the information to perform a CT study can be represented in an RIS database are as follows.

DICOM (ftp://medical.nema.org/medical/dicom/2008/08_16pu.pdf, Annex-D):
  112185 Performance of CT for Detection of Pulmonary Embolism in Adults.
  112186 Performance of High-Resolution CT of the Lungs in Adults.
CMS (Centers for Medicare and Medicaid Services) (http://www.cms.hhs.gov/ICD9ProviderDiagnosticCodes/06_codes.asp, Version 26 Effective Oct. 1, 2008, I-9 Procedures)
  3220 THORAC EXC LUNG LESION
  9215 PULMONARY SCAN
A hypothetical RIS site:

| | |
|---|---|
| CAT0346 | CT CHEST LUNG NODULE STUDY |
| CAT0001 | CT HEAD W/CONTRAST |
| CAT0415 | CT LUNG SCREEN |

Digital medical images are typically stored on a Picture Archiving and Communication System (PACS) for retrieval. PACS are computers or networks dedicated to the storage, retrieval, distribution and presentation of medical images. The medical images are stored in an independent format, the most common of which is the DICOM (Digital Imaging and Communications in Medicine) format. Most PACSs can handle images from various medical imaging instruments, including ultrasound (US), magnetic resonance (MR), positron emission tomography (PET), computed tomography (CT), endoscopy (ENDO), mammograms (MAMMO), digital radiography (DR), computed radiography (CR) etc. PACS systems are used to, inter alia, replaces hard-copy based means of managing medical images, such as film archives, and for providing capabilities of off-site viewing and reporting by enabling practitioners in different physical locations to access the same information simultaneously for teleradiology. A full PACS should provide a single point of access for images and their associated data (i.e. it should support multiple modalities), and should also interface with existing hospital information systems, such as the Hospital Information System (HIS) and Radiology Information System (RIS).

SUMMARY OF THE INVENTION

Exemplary embodiments of the invention as described herein generally include methods and systems for using an IHE-WL to enable a CAD system to determine what algorithms should be applied to a particular dataset.

According to an aspect of the invention, there is provided a computer implemented method for automatically selecting an algorithm for image analysis in a computer-aided detection/diagnosis (CAD) system, the method performed by the computer including receiving image data for a study involving a patient, querying a radiology information system (RIS) for an IHE (Integrating the Healthcare Enterprise)-worklist for the study of the patient, receiving the IHE-worklist from the RIS, analyzing the worklist to select one or more CAD algorithm for analyzing the image data, executing the selected one or more CAD algorithms to analyze the image data, and outputting results of the analysis of the image data.

According to a further aspect of the invention, the worklist is a text or word-processor document, and analyzing the worklist comprises performing a string search for one or more standardized codes for diagnostic procedures to be performed on the image data, and matching each standardized code to a diagnostic procedure to be executed on the image data.

According to a further aspect of the invention, the standardized codes are DICOM codes.

According to a further aspect of the invention, the standardized codes are CMS (Centers for Medicare and Medicaid Services) codes.

According to a further aspect of the invention, the standardized codes are custom codes for a particular imaging site, and the method includes configuring a CAD system with the diagnostic procedure codes prior to analyzing the IHE-worklist.

According to a further aspect of the invention, the method includes extracting info nation about prior studies of the patient from a picture archiving and communication system (PACS).

According to a further aspect of the invention, extracting information about prior studies of the patient comprises extracting whole body scans previously acquired from the same patient of a same modality as the image data, and executing the selected one or more CAD algorithms to track a lesion or tumor and determining whether the lesion or tumor is growing or shrinking, and at what rate the lesion or tumor is growing or shrinking.

According to a further aspect of the invention, the method includes searching for evidence of an associated illness in the image, based on a prior diagnosis.

According to a further aspect of the invention, searching for evidence of an associated illness comprises obtaining a patient admission date from a hospital information system, and searching for evidence of symptoms of pneumonia or a related illness in lung images of the patient.

According to a further aspect of the invention, the method includes, for a cancer patient, searching malignancy in common metastatic sites based on a prior cancer localization.

According to a further aspect of the invention, extracting information about prior studies of the patient comprises extracting images acquired from the patient using other modalities, and searching for other evidence of tumors or lesions in a body-part of interest.

According to another aspect of the invention, there is provided a computer-implemented method for automatically selecting an algorithm for image analysis in a computer-aided detection/diagnosis (CAD) system, the method performed by the computer including receiving from a radiology information system (RIS) an IHE (Integrating the Healthcare Enterprise)-worklist for an imaging study of a patient, where the worklist is a text or word-processor document, and analyzing the worklist to select one or more CAD algorithms for analyzing image data acquired for the patient by performing a string search for one or more standardized codes for diagnostic procedures to be performed on the image data, and matching each standardized code to a diagnostic procedure to be executed on the image data.

According to a further aspect of the invention, the method includes executing the selected one or more CAD algorithms to analyze the image data, and outputting results of the analysis of the image data.

According to another aspect of the invention, there is provided a program storage device readable by a computer, tangibly embodying a program of instructions executable by the computer to perform the method steps for automatically selecting an algorithm for image analysis in a computer-aided detection/diagnosis (CAD) system.

DETAILED DESCRIPTION OF EXEMPLARY EMBODIMENTS

Figure 1:
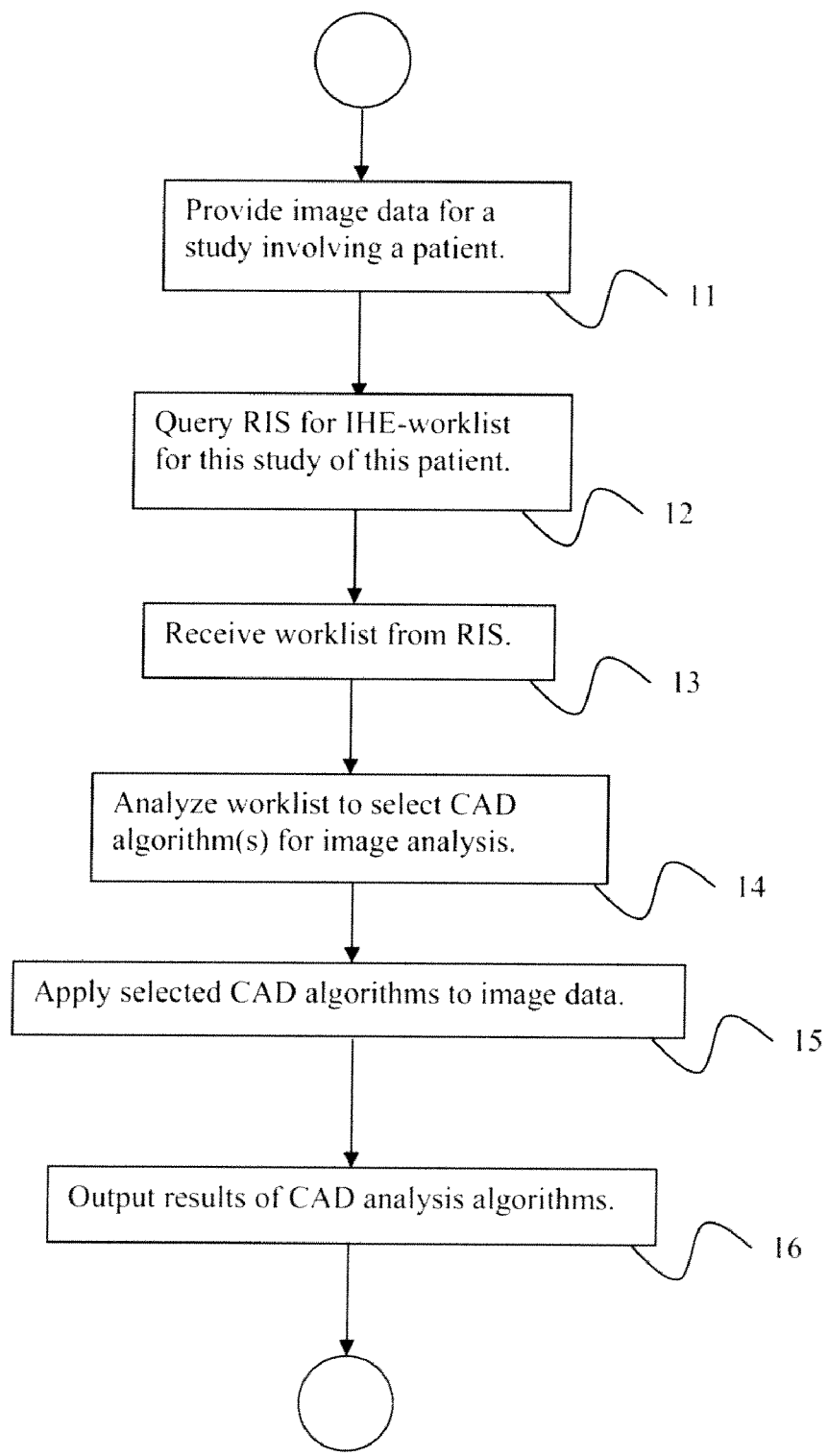
FIG. 1 is a flowchart of an exemplary method for using an IHE-WL to enable a CAD system to determine what algorithms should be applied to a particular dataset, according to an embodiment of the invention.

Exemplary embodiments of the invention as described herein generally include systems and methods for using an IHE-WL to enable a CAD system to determine what algorithms should be applied to a particular dataset. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

FIG. 1 is a flowchart of an exemplary method for using an IHE-WL to enable a CAD system to determine what algorithms should be applied to a particular dataset. Referring now to the figure, a method begins at step 11 by providing an image dataset to a CAD system for CAD processing. At step 12, the CAD system queries an RIS or equivalent system for a worklist, such as the IHE Scheduled Workflow, that would list the various procedure codes of the studies to be performed for this patient. At step 13, the CAD system receives the worklist data from the RIS or equivalent system. The worklist data would typically be a text or word processor document, and the CAD system can perform a string search of the document to search for procedure codes.

At step 14, based on the procedure entries in the worklist data, the CAD system can determine which algorithm or algorithms to apply to the image dataset. For example, the algorithm could be a lung CAD algorithm, a brain CAD algorithm, or a pulmonary embolism CAD algorithm, etc. For example, suppose a whole body CT image volume is the image dataset provided to the CAD System. If the procedure code read from the Scheduled Workflow is 112185 or 9215, then a pulmonary embolism (PE) CAD algorithm is executed. Similarly, if the procedure code read from the Scheduled Workflow is 112186 or 3220, then a lung CAD algorithm is executed. These procedure codes are referred to as fixed triggers. However, since not everyone uses these codes, it should still also be possible to specify a set of code(s) for which to run, e.g., a PE CAD algorithm or a lung CAD algorithm. This would be based on site specific business logic.

For example, expanding on the hypothetical RIS site disclosed above, the CAD system will need to be configured for the list of codes it should look for before doing lung CAD processing on a dataset. If the code is one of CAT0346 and CAT0415, then a lung CAD algorithm is processed for that dataset. If the code is CAT0001, then lung CAD processing is not performed for that dataset. However, if configured, other algorithms can be processed for this dataset, for example those consistent with WL code CAT0001, such as a head CT CAD algorithm.

The CAD system can also apply advanced decision support to gather information about prior studies from the PACS, i.e. extracting whole body scans previously acquired from the same patient, and applying the selected CAD algorithm to track if a lesion or tumor is growing or shrinking, and at what rate. Similarly, the CAD system, based on a prior diagnosis, can look for an associated illness in the image. For example, as in-patient pneumonia is a common occurrence in hospitals, the CAD system can obtain a patient admission date from the HIS and look for pneumonia symptoms in the patient's lung images. Similarly, for a cancer patient, based on a prior cancer localization, the CAD system can intelligently look for malignancy in common metastatic sites. In addition to looking for prior scans of the same modality, the CAD system can look for scans acquired from the patient using other modalities, such as positron emission tomography (PET), or magnetic resonance imaging (MRI), to look for other evidence of lesions in the body-part of interest.

At step 15, the CAD system runs the selected algorithms on the image dataset, and at step 16, the results from running the algorithms on the image dataset are output to the user or otherwise transmitted to other interested nodes.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 2:
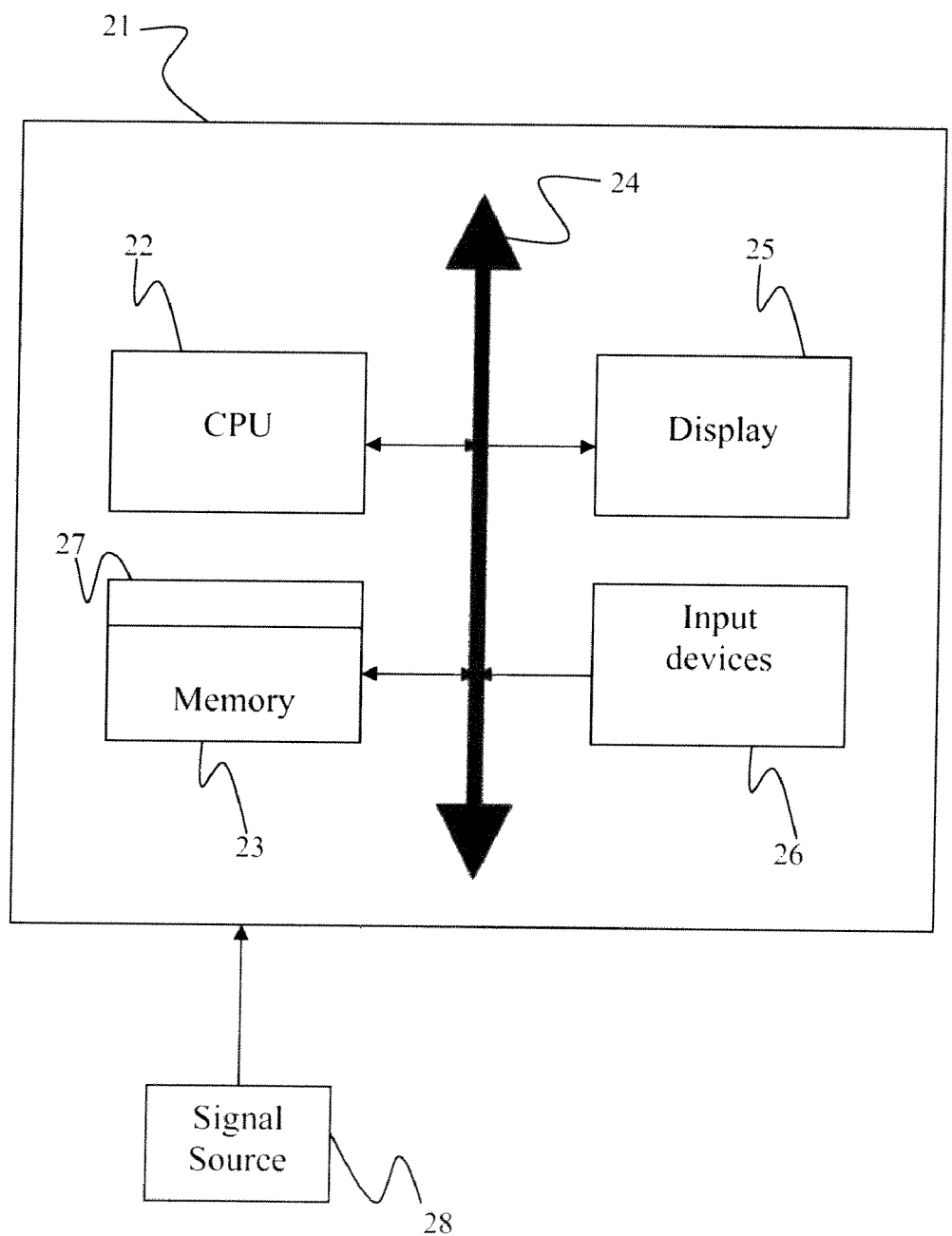
FIG. 2 is a block diagram of an exemplary computer system for implementing a method for using an IHE-WL to enable a CAD system to determine what algorithms should be applied to a particular dataset, according to an embodiment of the invention.

FIG. 2 is a block diagram of an exemplary computer system for implementing a method for using an IHE-WL to select an image analysis algorithm for use with a CAD systems according to an embodiment of the invention. Referring now to FIG. 2, a computer system 21 for implementing the present invention can comprise, inter alia, a central processing unit (CPU) 22, a memory 23 and an input/output (I/O) interface 24. The computer system 21 is generally coupled through the I/O interface 24 to a display 25 and various input devices 26 such as a mouse and a keyboard. The support circuits can include circuits such as cache, power supplies, clock circuits, and a communication bus. The memory 23 can include random access memory (RAM), read only memory (ROM), disk drive, tape drive, etc., or a combinations thereof. The present invention can be implemented as a routine 27 that is stored in memory 23 and executed by the CPU 22 to process the signal from the signal source 28. As such, the computer system 21 is a general purpose computer system that becomes a specific purpose computer system when executing the routine 27 of the present invention.

The computer system 21 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer-implemented method for automatically selecting an algorithm for image analysis in a computer-aided detection/diagnosis (CAD) system, the method performed by the computer comprising the steps of:
   receiving, by a computer system, image data for a study involving a patient;
   querying, by the computer system, a radiology information system (RIS) for an IHE (Integrating the Healthcare Enterprise)-worklist for said study of said patient;
   receiving, by the computer system, said IHE-worklist from said RIS;
   analyzing, by the computer system, said worklist to select one or more CAD algorithms for analyzing said image data, including searching the worklist for one or more standardized procedure codes and matching the one or more standardized procedure codes to the one or more CAD algorithms;
   executing, by the computer system, said selected one or more CAD algorithms to analyze said image data; and
   outputting, by the computer system, results of the analysis of said image data.

2. The method of claim 1, wherein said worklist is a text or word-processor document.

3. The method of claim 2, wherein said standardized codes are DICOM codes.

4. The method of claim 2, wherein said standardized codes are CMS (Centers for Medicare and Medicaid Services) codes.

5. The method of claim 2, wherein said standardized procedure codes are custom codes for a particular imaging site, and further comprising configuring a CAD system with said standardized procedure codes prior to analyzing said IHE-worklist.

6. The method of claim 1, further comprising extracting information about prior studies of said patient from a picture archiving and communication system (PACS).

7. The method of claim 6, wherein extracting information about prior studies of said patient comprises extracting whole body scans previously acquired from said same patient of a same modality as the image data, and executing said selected one or more CAD algorithms to track a lesion or tumor and determining whether said lesion or tumor is growing or shrinking, and at what rate said lesion or tumor is growing or shrinking.

8. The method of claim 6, wherein extracting information about prior studies of said patient comprises extracting images acquired from said patient using other modalities, and searching for other evidence of tumors or lesions in a body-part of interest.

9. The method of claim 1, further comprising searching for evidence of an associated illness in the image, based on a prior diagnosis.

10. The method of claim 9, wherein searching for evidence of an associated illness comprises obtaining a patient admission date from a hospital information system, and searching for evidence of symptoms of pneumonia or a related illness in lung images of said patient.

11. The method of claim 1, further comprising, for a cancer patient, searching malignancy in common metastatic sites based on a prior cancer localization.

12. A computer-implemented method for automatically selecting an algorithm for image analysis in a computer-aided detection/diagnosis (CAD) system, the method performed by the computer comprising the steps of:
receiving, by a computer system, from a radiology information system (RIS) an IHE (Integrating the Healthcare Enterprise)-worklist for an imaging study of a patient, wherein said worklist is a text or word-processor document; and
analyzing, by the computer system, said worklist to select one or more CAD algorithms for analyzing image data acquired for said patient by performing a string search for one or more standardized procedure codes, and matching each standardized procedure code to a CAD algorithm to be executed on said image data.

13. The method of claim 12, further comprising:
executing said selected one or more CAD algorithms to analyze said image data; and
outputting results of the analysis of said image data.

14. A program storage device readable by a computer, tangibly embodying a program of instructions executable by the computer to perform the method steps for automatically selecting an algorithm for image analysis in a computer-aided detection/diagnosis (CAD) system, the method comprising the steps of:
receiving, by a computer system, image data for a study involving a patient;
querying, by the computer system, a radiology information system (RIS) for an IHE (Integrating the Healthcare Enterprise)-worklist for said study of said patient;
receiving, by the computer system, said IHE-worklist from said RIS;
analyzing, by the computer system, said worklist to select one or more CAD algorithms for analyzing said image data, including searching the worklist for one or more standardized procedure codes and matching the one or more standardized procedure codes to the one or more CAD algorithms;
executing, by the computer system, said selected one or more CAD algorithms to analyze said image data; and
outputting, by the computer system, results of the analysis of said image data.

15. The computer readable program storage device of claim 14, wherein said worklist is a text or word-processor document.

16. The computer readable program storage device of claim 15, wherein said standardized codes are DICOM codes.

17. The computer readable program storage device of claim 15, wherein said standardized codes are CMS (Centers for Medicare and Medicaid Services) codes.

18. The computer readable program storage device of claim 15, wherein said standardized procedure codes are custom codes for a particular imaging site, and further comprising configuring a CAD system with said standardized procedure codes prior to analyzing said IHE-worklist.

19. The computer readable program storage device of claim 14, the method further comprising extracting information about prior studies of said patient from a picture archiving and communication system (PACS).

20. The computer readable program storage device of claim 19, wherein extracting information about prior studies of said patient comprises extracting whole body scans previously acquired from said same patient of a same modality as the image data, and executing said selected one or more CAD algorithms to track a lesion or tumor and determining whether said lesion or tumor is growing or shrinking, and at what rate said lesion or tumor is growing or shrinking.

21. The computer readable program storage device of claim 19, wherein extracting information about prior studies of said patient comprises extracting images acquired from said patient using other modalities, and searching for other evidence of tumors or lesions in a body-part of interest.

22. The computer readable program storage device of claim 14, the method further comprising searching for evidence of an associated illness in the image, based on a prior diagnosis.

23. The computer readable program storage device of claim 22, wherein searching for evidence of an associated illness comprises obtaining a patient admission date from a hospital information system, and searching for evidence of symptoms of pneumonia or a related illness in lung images of said patient.

24. The computer readable program storage device of claim 14, the method further comprising, for a cancer patient, searching malignancy in common metastatic sites based on a prior cancer localization.

* * * * *